(12) United States Patent
Genosar

(10) Patent No.: US 8,347,731 B2
(45) Date of Patent: Jan. 8, 2013

(54) FLOW RATE METER INCORPORATING REUSABLE DEVICE

(76) Inventor: Amir Genosar, Boulder, CO (US)

( * ) Notice: Subject to any disclaimer, the term of this patent is extended or adjusted under 35 U.S.C. 154(b) by 0 days.

(21) Appl. No.: 12/812,183

(22) PCT Filed: Jan. 8, 2009

(86) PCT No.: PCT/US2009/030499
§ 371 (c)(1),
(2), (4) Date: Oct. 4, 2010

(87) PCT Pub. No.: WO2009/089392
PCT Pub. Date: Jul. 16, 2009

(65) Prior Publication Data
US 2011/0185821 A1 Aug. 4, 2011

Related U.S. Application Data

(60) Provisional application No. 61/019,601, filed on Jan. 8, 2008, provisional application No. 61/019,600, filed on Jan. 8, 2008.

(51) Int. Cl.
*G01F 1/56* (2006.01)

(52) U.S. Cl. .................................................. 73/861.08

(58) Field of Classification Search ............... 73/861.08, 73/861.12, 861.16, 861.17
See application file for complete search history.

(56) References Cited

U.S. PATENT DOCUMENTS

| 4,195,515 | A | | 4/1980 | Smoll | |
|---|---|---|---|---|---|
| 4,346,604 | A | * | 8/1982 | Snook et al. | 73/861.12 |
| 6,505,517 | B1 | * | 1/2003 | Eryurek et al. | 73/861.08 |

OTHER PUBLICATIONS

International Searching Authority "Notification of Transmittal of the International Search Report and the Written Opinion of the International Searching Authority, or the Declaration" Feb. 17, 2009.

* cited by examiner

*Primary Examiner* — Jewel V Thompson
(74) *Attorney, Agent, or Firm* — Holland & Hart LLP

(57) ABSTRACT

A flow rate meter comprises a disposable fluid transport portion and a reusable interface connector removably attached to the transport portion. The transport portion includes a flow conduit having an input and an output, while the interface connector provides feedback to a desired location. First and second portions of control circuitry are, respectively, associated with the transport portion and the interface connector. The first circuitry portion includes a plurality of electrodes and derives flow rate. The device measures a range of flow rates and is adapted, for example, for use in micro-fluidic systems including fluids administration to a patient's body.

14 Claims, 8 Drawing Sheets

FLOW RATE METER INCORPORATING REUSABLE DEVICE

FIELD

The present invention relates generally to a device for monitoring mass flow rates. In particular the invention relates to an economically practical means for monitoring mass flow rates in a cost sensitive environment such infusion therapy.

BACKGROUND

Several advanced flow monitoring solutions have been invented over the years:

One such approach (Miller, Jr. et al., U.S. Pat. No. 4,532, 811) applies a thermal pulse to a stream of fluid and has a single downstream heat sensor to sense the thermal pulse. The transit time between the heating element and the heat sensor determines flow velocity. The Miller thermal pulse technique is effective over a wide range of fluid temperatures, because the unheated fluid is used as a reference: the downstream sensor detects thermal pulses, i.e. envelopes of fluid traveling through the flight conduit that are warmer than the unheated fluid. Therefore, the thermal pulse technique is advantageously insensitive to changes in ambient temperature.

Jerman, et al., U.S. Pat. No. 5,533,412 present an improvement to Miller's approach by providing at least two spaced apart sensors located along the flight conduit downstream from the thermal marking position and the flow velocity is derived from the time it takes the pulse to travel between two sensors.

Mosier, et. al., U.S. Pat. No. 6,660,675, and continuation in part Harnett, U.S. Pat. No. 7,225,683, disclose a device for measuring fluid flow rates over a wide range which operates by marking the fluid by producing compositional variations in the fluid (pulses), that are subsequently detected downstream from the marking position to derive a flow rate. Each pulse, comprising a small fluid volume, whose composition is different from the mean composition of the fluid, can be created by electrochemical means, such as by electrolysis of a solvent, electrolysis of a dissolved species, or electrodialysis of a dissolved ionic species. Measurements of the conductivity of the fluid can be used to detect the arrival time of the pulses, from which the fluid flow rate can be determined. A pair of spaced apart electrodes can be used to produce the electrochemical pulse mark.

To the knowledge of the inventor, none of the above inventions are believed to have resulted in practical commercial products, particularly for medical infusion where the medical tube sets are disposable, and integrating the above listed flow monitoring technologies in a disposable administration set is economically impractical.

U.S. Pat. No. 7,096,729 for Repko and al attempts to address the economical disadvantage of the above prior art by disclosing a disposable fluid flow sensor, which generally includes a flow channel assembly comprising a flow channel tube in association with a disposable flow channel portion. A sensor die is located proximate to a thin interface or membrane formed from the disposable flow channel portion, such that the sensor die measures a flow of fluid flowing through the flow channel tube and the disposable flow channel portion of the flow channel assembly. What Repko refers to to as a "disposable sensor" is actually a portion of a tube designed to externally receive a non-disposable sensor. In Repko's technology the sensor do not come in direct contact with the flow media (here after sometimes referred to as non-invasive vs. invasive) and therefore can introduce error due to a) variations in the flow conduit properties in particular those of the barrier (referred to as membrane in Repko's) between the sensor die and the flow media, b) variation in alignment between the flight tube and the sensor's die, c) user errors in replacing the sensor die appropriately and no means for detecting this error, and d) environmental effects such as dust or other contaminants, moisture and wetness, impressions of greasy fingers or talc from a nurse's gloves, e) loss of signal or information in the barrier (membrane) even at optimal operation conditions. Perhaps the most critical disadvantage of Repko's for critical flow measurement application such as medical infusion therapy is that an error or malfunction due to the above list of causes of errors can not be detected, and therefore can not be corrected for, while also can not alarm the medical staff.

Sage et al., U.S. Pat. No. 7,361,155 attempts to address some of the above disadvantages by disclosing a device that comprises a flow channel through which the liquid flows. During manufacture or at some other point prior to the delivery of the liquid, the flow channel is characterized in terms of one or more properties of flow of a liquid through the channel. This characterization is stored in such a way that the flow channel characterization is available to the liquid delivery device at time of use. At time of use, the liquid delivery system reads the stored flow channel characterization and uses the stored flow channel characterization for safe and accurate delivery of the liquid. While Sage' addresses the first disadvantage listed above for Repko's (marked as "a" in the previous paragraph) it fails to address the other disadvantages which are not related to manufacturing variations of the flow conduit. In particular Sage does not propose detecting and alarming for malfunction. More than anything, Sage's invention enlighten the problem need to be addressed to create an accurate and reliable device for measuring flows in disposable fluid transport systems which are economically practical. Sage's additional disadvantages is that calibrating each sensor, registering the calibration information on each individual sensor, and having delivery systems being equipped to read and process said registered information bare significant costs which are not desirable and usually not acceptable in medical care practices.

It is therefore the object to provide an economically practical flow measuring device for accurate and reliable flow monitoring in a fluid transport device.

It is another object to provide a flow measuring device that identifies human errors and malfunction and take measures to alarm a device or a person and to avoid harm or damage to a system, a patient, or a process or procedure.

It is another object to provide a flow measuring device that monitor flows in a fluid transport device in proximity to the outlet of said fluid transport device, and in particular where no possible disconnections may occur between the measuring position and the outlet of said fluid transport device.

It is another object to provide a flow measuring device that feedback to a flow control device which controls the flow in said fluid transport device, to improve the flow administration regime and to warn about hazardous conditions.

It is another object to associate a flow control device with the flow measuring device of the present invention.

It is another object of the present invention to provide safety means for preventing flow in the fluid transport device if the flow control device is suspected to malfunction.

SUMMARY

According to aspects of the disclosure, and as contemplated by the two diagrams below, a flow rate meter comprises a disposable (also referred to herein at times as "durable")

fluid transport device portion that a flow conduit having an inlet and an outlet, with the flow conduit defining a flow channel. The disposable portion also includes at least a first portion of a control circuitry which is operative to derive the flow rate, wherein the first portion includes a plurality of electrodes adapted to directly contact fluid when present within said conduit. A reusable interface connector removably attaches to the disposable fluid transport device portion. This connector includes a second portion of said control circuitry and a communications interface for establishing feedback communication to a desired location.

According to another aspect a flow measuring device (here after some times referred to as "flow meter") is provided for monitoring mass flow rates comprising: a) a portion of a fluid transport device, b) a durable device associated with the fluid transport device during the course of operation, c) a flow sensor, and d) electronic circuitry to operate said flow sensor where:

the portion of said fluid transport device comprises at least part of the flow sensor, the sensor comprises: a flow conduit associated with the flow media of the fluid transport device; at least part of the electronic circuitry (here after the "disposable circuitry") and is invasive to the flow media by at least two electrodes in direct contact with said flow media.

the durable device comprises at least part of the electronic circuitry (here after "durable circuitry")

The arrangement is such that:

The durable device operates the sensor and provides at least part of processing of the sensor signals to data, The durable device communicates said data with a device or a person.

The durable device can be reused when the fluid transport device is discarded.

The flow meter allows for economically practical and reliable implementation of a flow measurement in a disposable fluid transport device.

Further, the flow meter does not require calibration due to manufacturing variants or environmental conditions (as described above).

Yet further, the flow meter is not sensitive to mislocation or misalignment between the durable unit and the disposable unit, and can detect human errors or malfunction, and alarm, or take further actions due to that detection.

Yet further the flow meter does not suffer from losses of signal or information which non-invasive flow meters are sensitive to, associated with working through a barrier.

It also enables a small form factor, and thereby allows for locating the sensor in proximity to the desired position for reading the flow, for instance as in proximity to the injection site.

A system is also described for controlling mass flow rates in a fluid transport device comprising a flow meter as described above for measuring flow rates in said fluid transport device, and a flow control device for controlling the flow rates in said fluid transport device, wherein the data generated by the flow meter is used to adjust said flow by said flow control device.

The above arrangement allows for economic practical implementation of a medication infusion system. It also allows for locating the sensor in proximity to the desired position for reading the flow, such as in proximity to the injection site.

Monitoring flow rates generally refers to precise measurement of flow rates as well as precisely sensing the existence or absence of flow.

Several mass flow metering technologies are applicable for the present invention:

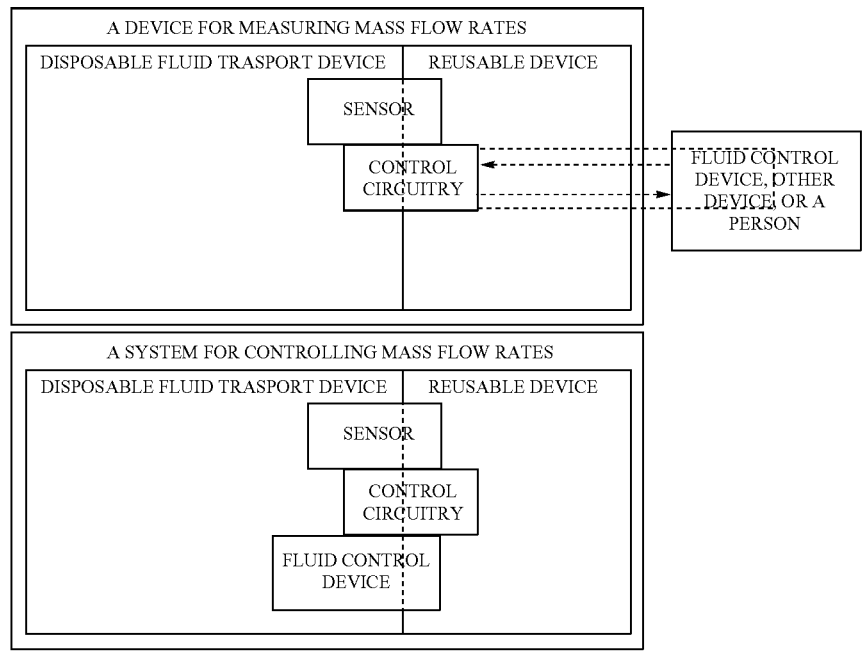

The durable device (also interchangeably referred to herein as a reusable device or portion) can comprise part of a system such as a kit including a non-disposable portion and two or more disposable portions In one preferred embodiment the flow meter is a Composition Variation Time-Of-Flight (TOF) Mass Flow Meter (MFM) as disclosed by U.S. Pat. No. 6,660,675 and U.S. Pat. No. 7,225,683, incorporated here by reference. These TOF MFMs refer to a device for measuring fluid flow rates which operates by marking the fluid by producing compositional variations in the fluid, or pulses, that are subsequently detected downstream from the marking position to derive a flow rate. Each pulse, comprising a small fluid volume, whose composition is different from the mean composition of the fluid, can be created by electrochemical means, such as by electrolysis of a solvent, electrolysis of a dissolved species, or electrodialysis of a dissolved ionic species. Measurements of the conductivity of the fluid can be used to detect the arrival time of the pulses, from which the fluid flow rate can be determined. A pair of spaced apart electrodes can be used to produce the electrochemical pulse mark, while another pair of electrodes can be used for detection of the pulse.

The mass flow rate meter could also be constructed according to any of the embodiments described in my co-pending U.S. application Ser. No. 12/350,897 filed Jan. 8, 2009, or my co-pending PCT application Serial No. PCT/US09/30494, also filed on Jan. 8, 2009. These applications are also incorporated in their entireties.

The fluid transport device generally refers to any means for communicating fluid media between a source or a number of sources and a target or a number of targets. The fluid transport device may comprise a hose, a tube, a pipe, a fitting, a connector a wick, a channel, a conduit, a groove, a trench, an enclosed path machined in a circuit board a chip or a wafer, a device implemented in the flow path communicating the upstream and the down stream portions of the fluid transport device, a port, a nozzle, a spout, a needle, a canula, a combination of the above or any other means known in the art. The fluid transport device can be connected to additional fluid transport devices.

In one preferred embodiment of the present invention the above composition Time-Of-Flight is implemented by incorporating a disposable flight conduit section in the fluid transport device. The flight conduit establishes fluid communication between two portions of the fluid transport device. The flight conduit comprises at least a portion of the disposable circuitry comprising at least two pairs of invasive electrodes in direct contact with the flow media—one pair for generating the mark and another pair spaced apart downstream from the first pair for detecting the mark. In one embodiment one electrode of each pair of electrodes is common thus reducing the actual number of electrodes to three. The disposable circuitry is associated with the durable (i.e. reusable) circuitry by communication channels and/or powering channels. In one embodiment contact tabs extend from said portion of said fluid transport device which come in contact with the durable device to associate said disposable circuitry with said permanent circuitry. In another embodiment said association is wireless. In one embodiment the disposable circuitry is merely the sensor electrodes and conductive traces communicating said sensor electrodes with said contact tabs to the durable device. In another embodiment the disposable circuitry comprises filters and/or other elements to modulate, clean, or partly process the signals. In another embodiment the disposable circuitry comprises an RFID circuit. In a further embodiment the RFID circuit is used to power and/or communicate signals and data. In one embodiment said disposable circuitry comprises an element that identifies that the fluid transport device has been previously in use, such as a fuse that is burned during the first operation of the flow meter. The durable device comprises the circuitry for operating said electrodes, optionally processing the sensor signals, and communicating said signals or data to a person or a device.

In one embodiment said data is communicated to a display panel such as a seven-segment display, an LCD display, a video monitor, etc. In one embodiment said display is integrated in the durable device. In another embodiment the durable device comprises visual and/or audible communication means with a person (such a LED and/or buzzer) providing flow rates values, information on the functionality of the system as well as warning indications.

In another embodiment the data is communicated to a flow control device which controls the flow in said fluid transport device, to enhance the control of the flow rates in a closed-loop control fashion, or to warn of hazardous conditions. Said communication means can be (but is not limited to) one of the communication means known in the art including RF, IR, Ultrasonic, or hard wired. In one embodiment said communication wires are integrated in the tube of the fluid transport device such as by co-extrusion. Flow control devices include, but are not limited to: peristaltic pumps, syringe pumps, pressurized bladders (balloons) with controllable flow restrictor, or gravitational delivery with flow restrictor, or any other flow control devices known in the art.

In one embodiment said flight conduit is a segment of a tube of the fluid transport device. In another embodiment the flight-conduit is a fitting inserted between two segments of the fluid transport device. In another embodiment the flight conduit is implemented in the peristaltic pumping portion of a dedicated peristaltic pump set. In another embodiment the flight tube is implemented in the exit port of a syringe, an infusion bag, infusion bottle, or similar device. In one embodiment the flight conduit is implemented in an infusion bag/bottle spike. In another embodiment the flight conduit is implemented in a portion of an invasive device (such as a needle or catheter) thereby further reducing the risk of discrepancies between the actual flow delivered from the fluid transport device and the measured values, and in particular reduces the risk of such discrepancies due to disconnections in the fluid transport device due to human error, kinks in the tube, occlusion of the administration device, etc.

In one embodiment, this invention represents a system comprising a kit, which includes one durable device and at least two fluid transport devices. In such a kit, the fluid transport device may be the same, or may be different from each other. In a preferred embodiment, the durable device comprises the user interface and control electronics of the system.

In one embodiment the system comprises at least two disposable components comprising flow channels that are different from each other. In a preferred embodiment, these channels differ in design, so that they may, for example, be optimized in geometry to measure different ranges of flow rate.

In a further preferred embodiment, these flow channels comprise means for identifying one design from another without involvement from the user. In one example, the channels comprise tabs that make electrical contact to a non-disposable component, and the specific geometry of the tabs serve in part to establish the identity of the disposable component. These tabs may be electrically connected to the sensing or write electrodes, or they may be electrically isolated from the channel electrodes. In one embodiment, the tabs are isolated from the channel electrodes, and when in contact with the non-disposable component close a specific circuit on the non-disposable component that verifies the channel's identity.

In one embodiment additional detectors are incorporated in the flow meter, for example: temperature, pressure, shock (G), air bubbles detector, specific mass detector, concentration detector, or other detectors known in the art. In one embodiment the flow meter provides at least part of the components for said additional detectors. In another embodiment at least part of the flow meter is incorporated in another detector or device. In one embodiment, the flow sensor is implemented in a chip which incorporate other electronic sensors.

In one embodiment the flow meter is incorporated in a flow control system that comprises means for shutting-off the flow in the fluid transport device. In one embodiment at least part of said flow stopping means is incorporated in the fluid transport device. In one embodiment at least part of said flow stopping means is incorporated in the durable device. In one embodiment the flow stopping means is a pinch valve which has a movable rigid section that can be advanced to press on a flexible tube portion of the fluid transport device, thereby causing said tube portion to collapse and shut off the fluid passage. In another embodiment the flow-shutoff is a normally closed valve and the flow control device manipulates said valve to open. The flow shut-off means can be activated if malfunction of the fluid transport device is suspected or detected. In another embodiment the flow control device is incorporated in the flow meter.

In one embodiment the flow meter is incorporated in a flow control system that comprises means for regulating the flow in the fluid transport device. In one embodiment at least part of said flow regulating means is incorporated in the fluid transport device. In one embodiment at least part of said flow regulating means is incorporated in the durable device. In one embodiment the flow regulating means is a pinch valve which has a movable rigid section that can be advanced to press on a portion of a flexible tube of the fluid transport device, thereby causing said tube portion to collapse and narrow down the fluid passage, thereby limiting the flow in the fluid transport device. In another embodiment the flow regulating means is a normally closed valve which is manipulated by the flow control device to proportionally open. In one embodiment the durable device can be set to a desired flow rate and maintain said rate accordingly. The flow regulating means is particularly advantageous where the flow control device is merely an infusion bag or a balloon (together "passive infusion devices"). In one embodiment a Human Machine Interface (HMI) panel allows for setting of the desired flow rates for said flow regulator and alerting conditions at which alarms will be activated and the flow through said flow regulator will be halted.

The durable device can be powered by one of the means known in the art including, but not limited to: AC wall power, DC, battery, a rechargeable battery, a photovoltaic cell, a motion activated power generator, RF induction, RFID circuit or a combination of the above. In one embodiment the durable device is operated (powered) by wires which are embedded in the tubing of the fluid transport device. In one embodiment said embedded wires are fed from a power source in the flow control device. In another embodiment the flow control device is an infusion pump and the fluid transport device is an infusion set, and said durable device is operated by a rechargeable battery, where said flow control device comprises a dock for recharging the battery of the durable device.

In a further embodiment the present invention comprises means for preventing loss of the durable device pre- or post-use. In this embodiment the durable device and/or the fluid control device comprises means for sensing the distance range of one from another and a warning means to inform a person (visual and/or audible) or a device that the durable device is too far removed from the flow control device.

The flow meter is not sensitive to miss-location or mis-alignment of the durable device and the fluid transport device and as long as the communication between the durable circuitry and the disposable circuitry exists the accuracy of the measurement is not biased, not effected by environmental conditions, not effected by human errors, and does not require calibration. Lack of communication between the durable circuitry and the disposable circuitry can be immediately and reliably detected and immediate measures can be executed to avoid harm or damage to a system, patient, process or procedure

DETAILED DESCRIPTION OF THE INVENTION

Figure 1A:
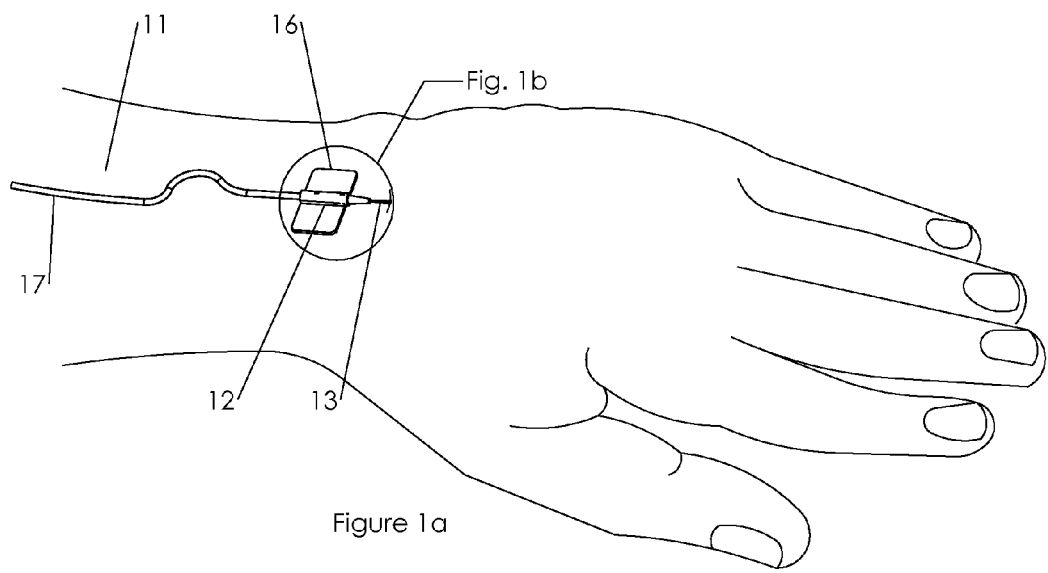
FIGS. 1a-1j each illustrate aspects of a preferred embodiment of the device of the present invention where the fluid transport device is an IV (intravenous) tube set.

Referring to FIG. 1a, a fluid transport device 11 is shown, in the fashion of an IV catheter set. The fluid transport device 11 comprises a tube 17 terminating in a catheter hub 16. The catheter hub 16 is connected to a fluid administration catheter 13 commonly in the form of a stainless steel hypodermic needle or a soft cannula. The catheter hub comprises a flight conduit 12 having a first end in fluid communication with said tube 17, and a second end in fluid communication with said catheter 13, said flight conduit 12 establishes a permanent fluid communication between the tube 17 and the catheter 13. Said flight conduit 12 provides portion of a TOF MFM. The tube 17 establishes a fluid communication between the flight conduit 12 and a flow control device (not shown) which controls the delivery rates (flow rates) of a medication from a fluid source. Said flow control device can be any of the flow control devices known in the art including an infusion bag with a flow regulator, a pressurized bladder (balloon), a peristaltic pump, a syringe pump, micro-infusion devices, a MEMS micro fluidic pump, Osmotic pump, a syringe, etc. The tube 17 can be connected to the hub 12 by pressure fit, barb fitting, glue, heat sealing, Luer slip connector, Luer lock connector, etc.

Figure 1B:
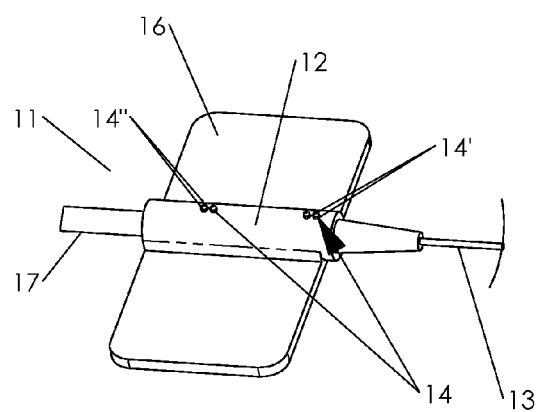

The detail view in FIG. 1b shows the hub 16 of FIG. 1a. The hub 16 comprises a portion of a Composition-Variation TOF MFM according to the operation principal disclosed by U.S. Pat. No. 6,660,675 and U.S. Pat. No. 7,225,683 incorporated here by reference in their entireties. Two pairs of electrodes 14 are accommodated in the flight conduit 12 wall having a first end in contact with the fluid in the flight conduit (not shown) and a second end extending through the conduit wall to form connector tabs to the durable device (not shown). The first pair of electrodes 14' is accommodated at a first position along the flight conduit 12 (also referred to as "introduction location"), and is used as the excitation electrodes or mark generator, and the second pair of electrodes 14", accommodated spaced apart downstream from the first pair 14', capable of detecting said mark. The flow rate is analyzed from the transient (or "flight") time of the mark between the excitation time at the first electrodes 14' and the detection time by second pair of electrodes 14", the distance between the first pair 14' and the second pair 14" of electrodes, the fluid properties, and the cross section of the flight conduit 12. In one embodiment an electric pulse to the first pair of electrodes 14' creates composition variation by ionizing or oxidizing a dissolved species in the fluid. The detection electrodes 14" will sense the variation by measuring oxidation-reduction current. It is therefore important to maintain accurate physical dimensions of the features that affect the flow rates analysis. In one embodiment the hub 16 is injection molded from a thermoplastic material such as PE, and the electrodes 14 are insert-molded into the flight conduit 12 at precise locations. In another embodiment the flight conduit 12 and the electrodes 14 are embedded in a silicon or glass chip which is accommodated in the fluid transport device 11.

Other flow measuring principals are applicable including Thermo-Time-Of-Flight mass flow meter, electronic flow switches, mechanical velocity meters, etc.

Figure 1C:
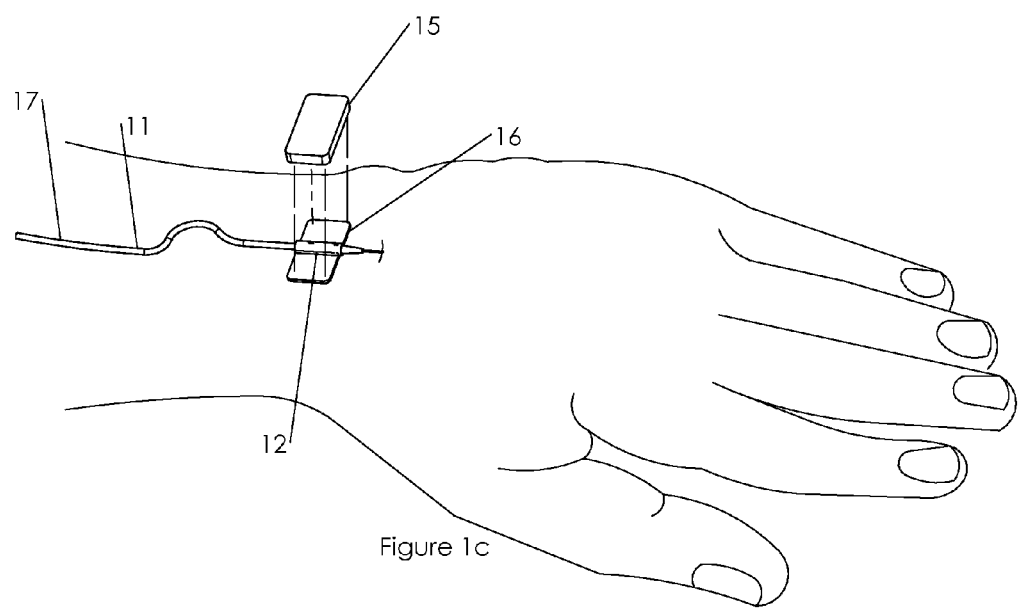

Referring now to FIG. 1c the fluid transport device 11 of FIG. 1a is shown together with a durable device 15, shown in a displaced position from the hub 16. The durable device 15 comprises a package and at least part of the electronic circuitry for operating the sensor and for communicating the measurements data with a person or a device, and tabs for electrically connecting to the tabs of the electrodes 14 in the hub 16. In one embodiment the durable device generates the electric pulse at the first electrode couples 14' to generate a composition variation mark in the flow. In one embodiment the durable device 15 operates the second pair of electrodes 14" for electroanalytically detecting the arrival of the mark. The circuitry of the durable device 15 will monitor current between the second pair of electrodes as an indication of a change in conductivity which indicates the arrival of the mark. In some embodiments the durable device is powered by a rechargeable battery. In one embodiment the flow control device (not shown) comprises a recharge docking station for the durable device. In another embodiment the device comprises at least two rechargeable-battery operated durable devices such that at least one durable device 15 can be recharged while another durable device 15 is in use. In another preferred embodiment of the present invention the durable device is powered by wires. In one embodiment said wires are embedded in the fluid transport device leading from an electric power source in the flow control device to the hub 16 and terminating with connector tabs along side the electrode's 14 tabs. Alternatively the durable device can be powered by several other means known in the art including photovoltaic cells, motion converter, capacitor, or RF energy for example RF energy received by an RFID circuit, etc.

In one embodiment the durable device and the fluid control device are equipped with distance range detector and a warning circuitry in case that the distance between the durable device 15 and the flow control device exceeded a predefined distance, for example to prevent accidental discard or loss of the durable device in particular when the fluid transport device 11 is disposable and is intended to be discarded at the end of a medical procedure. In another scenario said out-of-range arrangement alerts an unintentional/accidental disconnect of at least part of the fluid transport device which is connected to the patient from the flow control system.

Figure 1D:
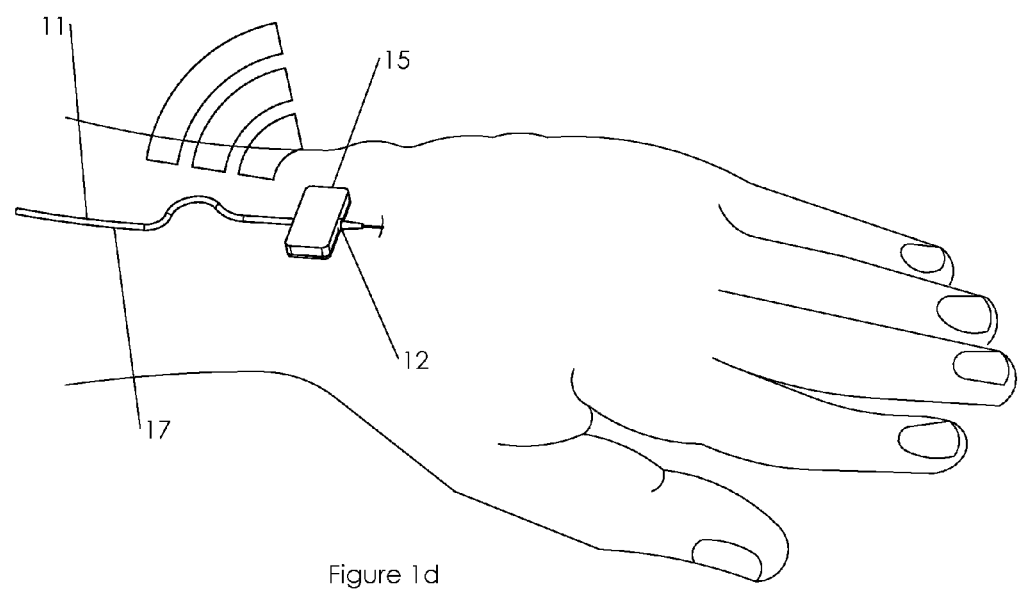

Referring now to FIG. 1d, the preferred embodiment of FIG. 1c is shown where the durable device 15 is attached to the fluid transport device 11, and is operating. The figure illustrates a wireless transmission from the durable device 15 to the flow control device (not shown). The durable device can transmit actual flow rate values or raw or semi-processed data to be processed by another device. In some configurations the durable device can be communicated-to for example for the purpose of self-testing, setting alarm values, or setting the flow meter to a specific flow rates range.

The durable device 15 is attached to the fluid transport device by one or more of the means known in the art including mechanical snap engagement, rotation, quarter turn, adhesive, adhesive tape, screws, thread, tongue and groove, magnetic coupling, etc.

The communication means can be one or more of the means known in the art including RF, IR, magnetic induction, ultrasonic, or by-wires. In one embodiment of the present invention the wire communication between the flow control device and the durable device 15 is through wires embedded in the fluid transport device 11 leading from the flow control device to the hub 16 and terminating with connector tabs along side the electrode's 14 tabs. In one embodiment same wires are used for powering the durable device 15 and communicating between the durable device 15 and the flow control device.

The communication protocol of the durable device can include identification of the durable device 15 to avoid influence of other durable devices active in the range from interfering.

Figure 1E:
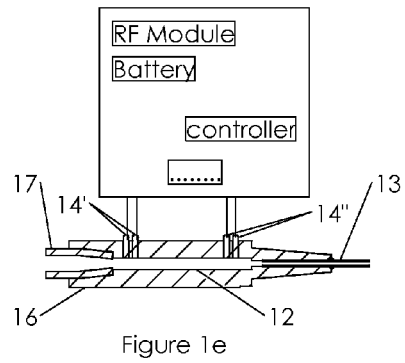

Referring now to FIG. 1e a section view of the hub 16 is demonstrated with a schematic presentation of the general functional circuitry of the durable device 15. The electrodes 14 are reaching through the wall of the flight conduit 12 to contact the fluid. The distal end of the electrodes 14 are in contact with the circuitry of the durable device 15. In one preferred embodiment a functional level layout of the durable device 15 comprises a 'female' connector for communicating with a 'male' connector in the hub 16, a controller, and a RF module for communicating with a flow control device.

Figure 1G:
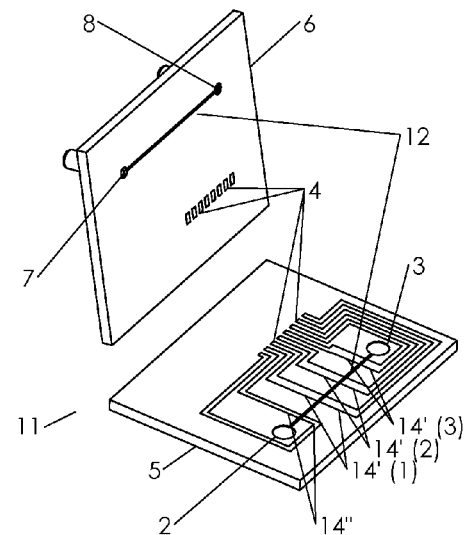
Figure 1F:
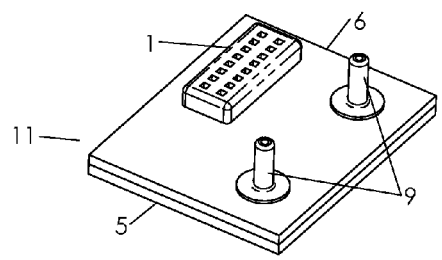
Figure 1I:
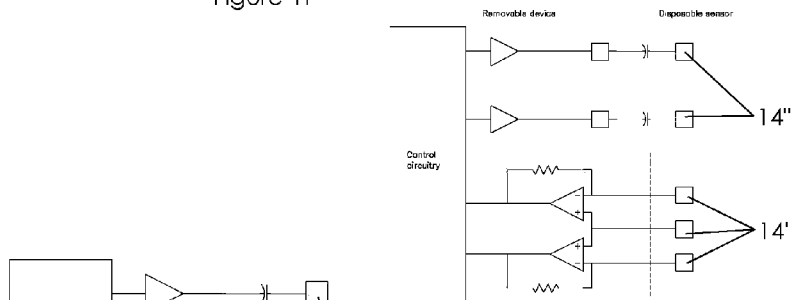
Figure 1H:
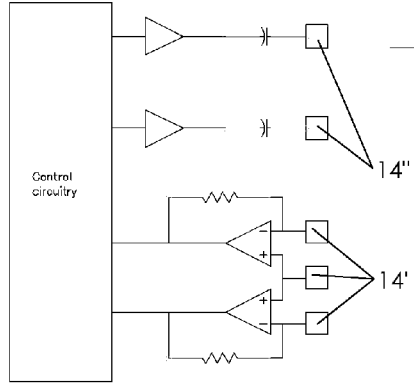
Figure 1J:
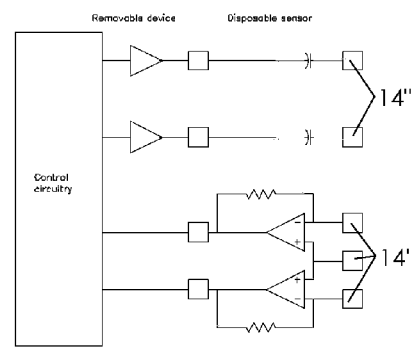

Referring now to FIG. 1h a circuit topology of the durable device 15 is demonstrated. A sinusoidal waveform, with an amplitude between 0.01-1.0 volts, is applied at a frequency of 30 Khz to drive terminals of a specific geometry. The fluid responds based on its impedance, where the impedance response of the fluid incorporating a marker is different from the reference response. The control circuitry can be more difficult to dispose of due to cost and regulatory requirements.

The geometry of the flow conduit 12 and the sensor electrodes 14" can accommodate a wide range of flow rates and fluid chemistry. Different modules for specific flow detection applications can be accommodated. Such modules can be patterned with a series of identifiers such as electrical contacts that can be automatically recognized by the durable device of the flow system.

Referring now to FIGS. 1f and 1g, an implementation of the circuitry of the disposable device in a PCB is demonstrated. FIG. 1f demonstrates the assembled position of the PCB having inlet an outlet nipples connecting to the fluid transport device (not shown). A connector 1 is disposed on the surface of the sensor 11 for connecting the durable device (not shown). Two major layers of the PCB are demonstrated 5 and 6. FIG. 1g demonstrates an exploded view of the PCB 11. A flow channel 12 is disposed between inlet cavity 2 and outlet cavity 3. Inlet cavity 2 is in fluid communication with the inlet 7 which communicates with the nipple 9. Outlet cavity 3 is aligned and in fluid communication with outlet 7 which is in fluid communication with a nipple 9. Conductive pattern 4 is printed on the substrate layers 5 and 6 electrically communicate the connector and the electrodes 14' and 14" which are in fluid communication with the flow conduit 12. In some embodiment further electronic and electric components are embedded in the sensor circuitry as will be exemplified in the following figures. In some embodiments the fluid channel is interconnected with other fluidic devices which are embedded in or disposed over the PCB assembly. It will be obvious to those skilled in the art that similar arrangement can be accomplished on a substrate such as in silicon, glass, or plastic. In one embodiment such circuitry is integrally produced by thin film chip manufacturing techniques.

Referring now to FIG. 1$i$, a further preferred circuit topology for the embodiment of FIG. 1 is demonstrated.

In this embodiment the disposable circuitry comprises isolation circuitry as part of the disposable fluid transport device, and the durable circuitry in the durable device comprises a control and processing circuitry separated. Isolation provided by capacitive means is inexpensive and compact, hence can be included in the disposable module.

Referring now to FIG. 1$j$, a further preferred circuit topology for the embodiment of FIG. 1 is demonstrated. In this embodiment the disposable circuitry comprises isolation circuitry and sense amplifiers which are integrated into the disposable fluid transport device. This arrangement reduces noise and allows the control circuitry in the durable circuitry to be located farther away from the disposable circuitry.

Figure 2A:
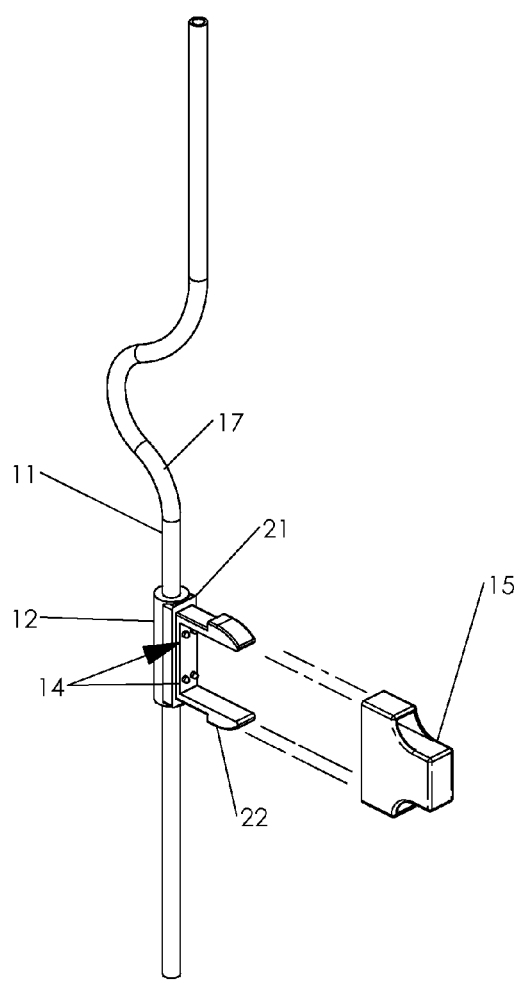
FIGS. 2a & 2b demonstrate a preferred embodiment where part of the sensor is accommodated in a fitting in the fluid transport device.
Figure 2B:
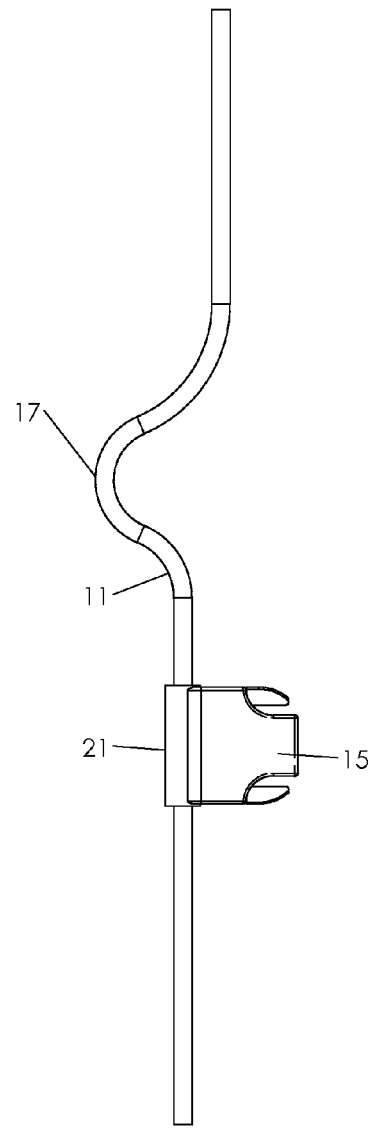

Referring now to FIG. 2, another preferred embodiment is shown where the flow meter is a Composition-Variation-Time-Of-Flight mass flow meter and where the flight conduit is implemented in a tube fitting 21, connecting between two portions of a tube 17 of the fluid transport device 11. FIG. 2$a$ shows the durable device 15 removed from the fitting 21. The electrodes tabs 14 are clearly seen as well as the snap feature 22 of the fitting 21, for engaging the durable device 15. FIG. 2$b$ shows the embodiment of FIG. 2$a$ where the durable device 15 is engaged with the fitting 21 in the operable position.

Figures 3A, 3B:
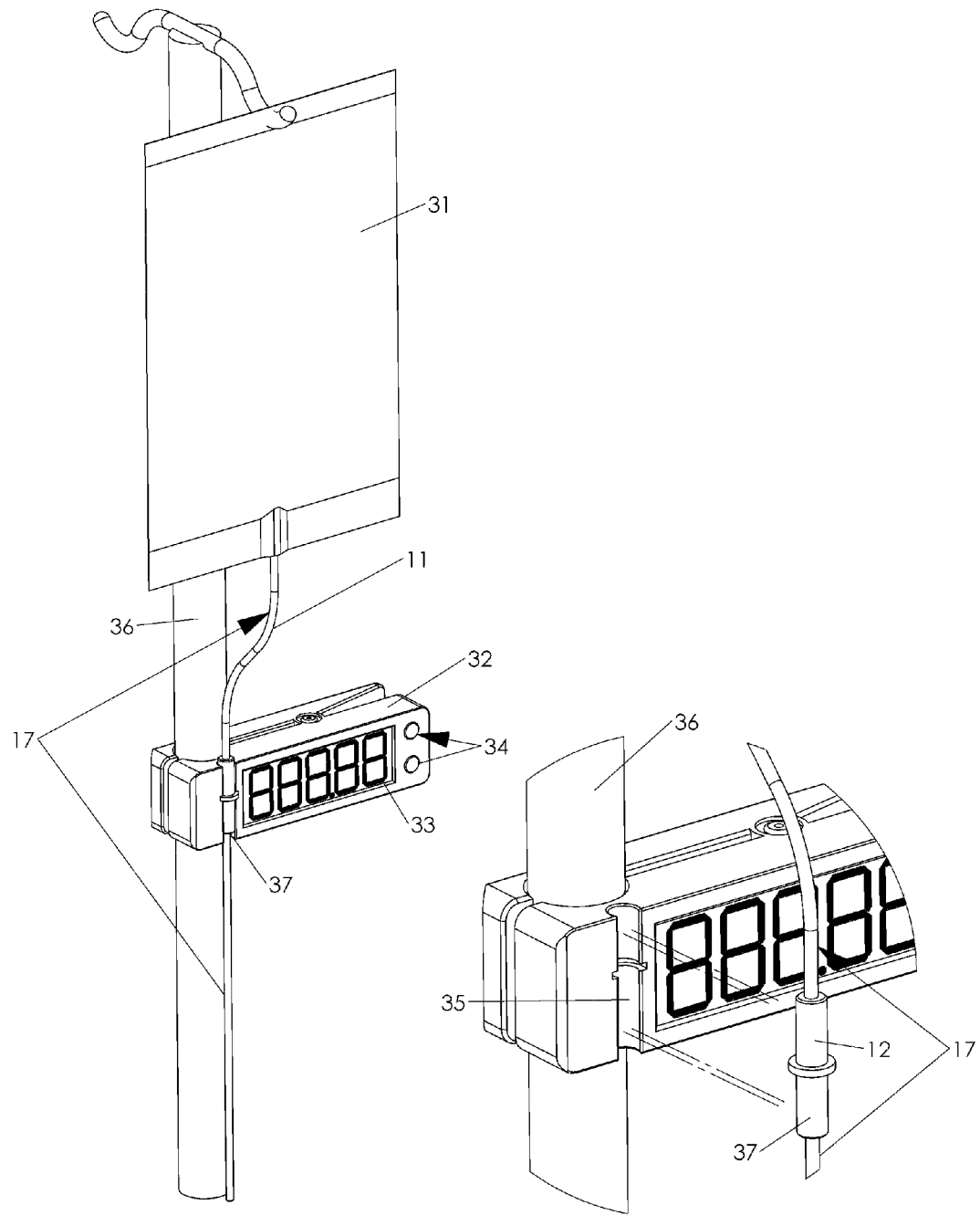
FIGS. 3a & 3b demonstrate a durable device comprising HMI, and a flow regulator.

Referring now to FIG. 3, a further preferred embodiment is demonstrated, where the flow meter is a Composition-Variation-Time-Of-Flight mass flow meter and where the flight conduit 12 is implemented in a tube fitting 37, connecting between two portions of a tube 17 of the fluid transport device 11. The durable device 32 comprises means for attaching to an infusion pole 36 in a form of a clamp, and includes a Human Machine Interface (HMI).

The HMI of the durable device 32 comprises a seven segment display 33 which shows the flow rate and other indications. The HMI further comprises buttons 34 for setting parameters and functions of the durable device 32 such as, units of measure to display, set or reset time of the procedure, set or reset accumulated dose of the treatment, enter flow rates alarm values, reset alarms, view statistics, scroll between functions, etc.

The HMI can further comprise visual and audible indications such as LED lights, buzzer, speaker or other means known in the art.

In one embodiment the durable device 32 can receive information from other devices such as additional sensors, or information from the flow control device and display this data.

In one embodiment the durable device 32 comprises means for shutting-off the flow in the fluid transport device. In one embodiment at least a portion of said flow shut-off means is incorporated in the fluid transport device 11. In one embodiment the flow stopping means is a pinch valve (not shown) which has a movable rigid section that can be advanced to press on a flexible tube portion of the fluid transport device, thereby causing said tube portion to collapse and shut down the fluid passage. The flow shut-off means can be set to be activated if a suspect of malfunction in the flow control device has been detected. Said movable part can be manipulated by a motor, a motor and a gear, piezo actuator, a solenoid actuator, a spring, a combination of those or any other means known in the art.

In one embodiment the durable device 32 comprises means for regulating the flow in the fluid transport device 11. In one embodiment at least portion of said flow regulating means is incorporated in the fluid transport device 11. In one embodiment the flow regulating means is a pinch valve (not shown) which has a movable rigid part that can be advanced to press on a portion of a flexible tube of the fluid transport device, thereby causing said tube portion to collapse and narrow down the fluid passage thereby limiting the flow rates. Said movable part can be manipulated by a motor, a motor and a gear, piezo actuator, a solenoid actuator, a spring, a combination of those or any other means known in the art. The circuitry in the durable device 32 will set the flow restrictor according to the flow rates measurements establishing a closed-loop control of the flow rates. The durable device can be set to a desired flow rate using the HMI or other communication means with the durable device 15, and maintain said rate accordingly. The flow regulating means is particularly advantageous where the flow control device is merely an infusion bag and where the fluid is biased to the fluid transport device by merely gravitational force, or pressurizing means applying pressure to said infusion bag.

In one embodiment the durable device 32 is powered by a wall AC supply, adjusted by internal or external power converter.

In one embodiment the fluid transport device comprises an individual identification means (ID) and the durable device comprises means for identifying said ID. The identification means can be a barcode or RFID or any other identification means known in the art. The identification can be used to prevent reuse of a disposable fluid transport device 11. The identification means can also identify compatibility of a fluid transport device 11 to a particular administration application.

Figure 4A:
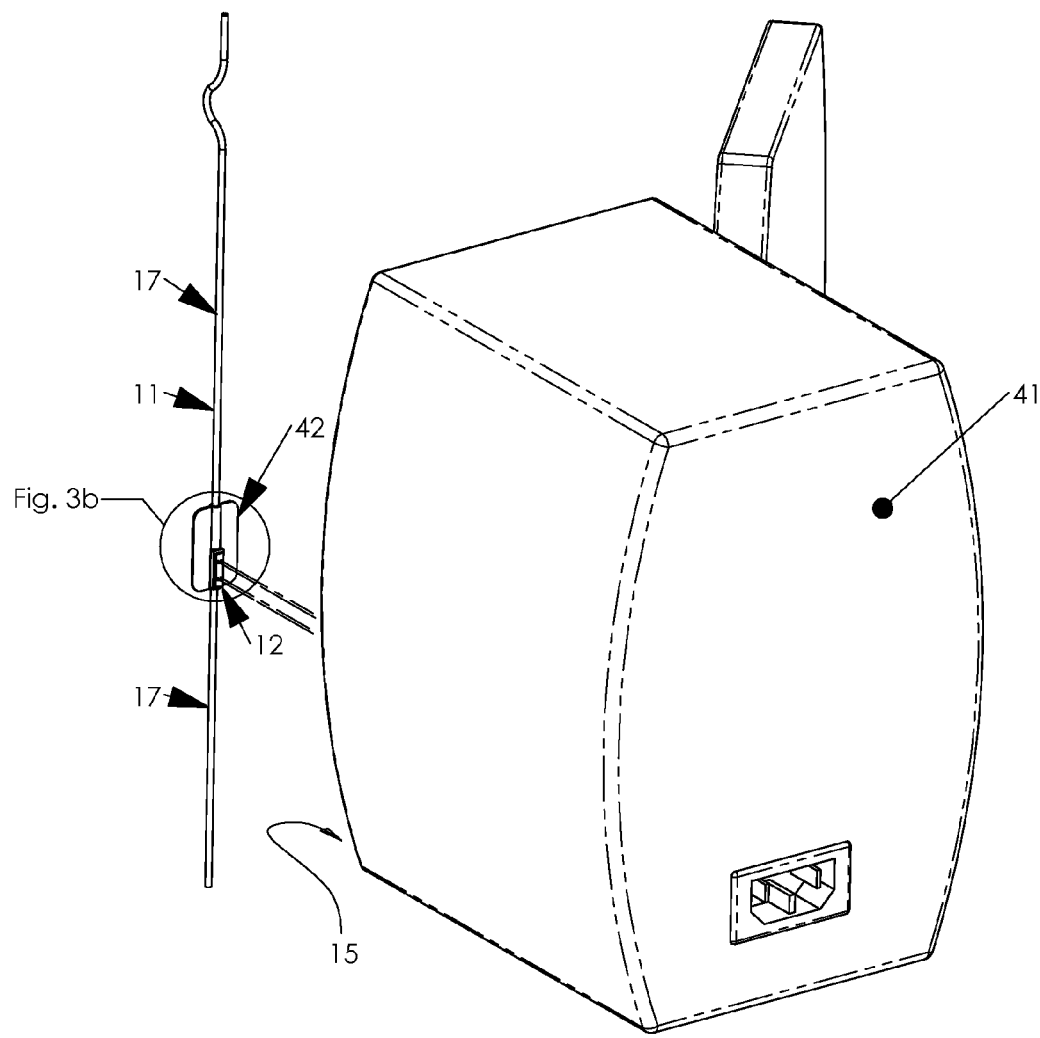
FIGS. 4a & 4b demonstrate a preferred embodiment where the durable device is accommodated in a drug delivery pump.
Figure 4B:
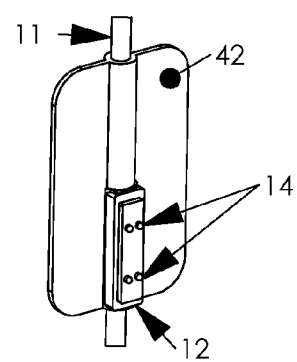

Referring now to FIG. 4$a$ another preferred embodiment of the present invention is demonstrated where the fluid transport device 11 is a dedicated tubing set for a peristaltic infusion pump 41. The infusion set 11 comprises a dedicated pumping portion 42 integrated between two tube sections 17 of the fluid transport device 11, said pumping portion communicates with the pump 41 and is manipulated by the pump to advance fluid from a reservoir (not shown) to the administration means to the body of a subject (not shown). The principal of operation of the flow meter in this embodiment is a Composition-Variation TOF MFM as described in FIG. 1, and its flight conduit 12 is preferably accommodated on the same platform as the pumping portion 42. The durable device is incorporated in the pump and is engaged with the tabs 14 when the pumping feature 42 is engaged with the pump 41. The durable device communicates with the pump circuitry to improve pumping accuracy. In one embodiment the durable circuitry is implemented in the pump circuitry.

In one embodiment the data from the durable device 15 is used for self diagnosis and self calibration of the flow control device 42. In one embodiment the program of the flow control device comprise a routine for performing self calibration or self diagnosis of the pump. In another embodiment the diagnosis routine can be remotely activated by a technician or a device. The last arrangement can contribute to a significant cost reduction of operation and maintenance.

Figure 5A:
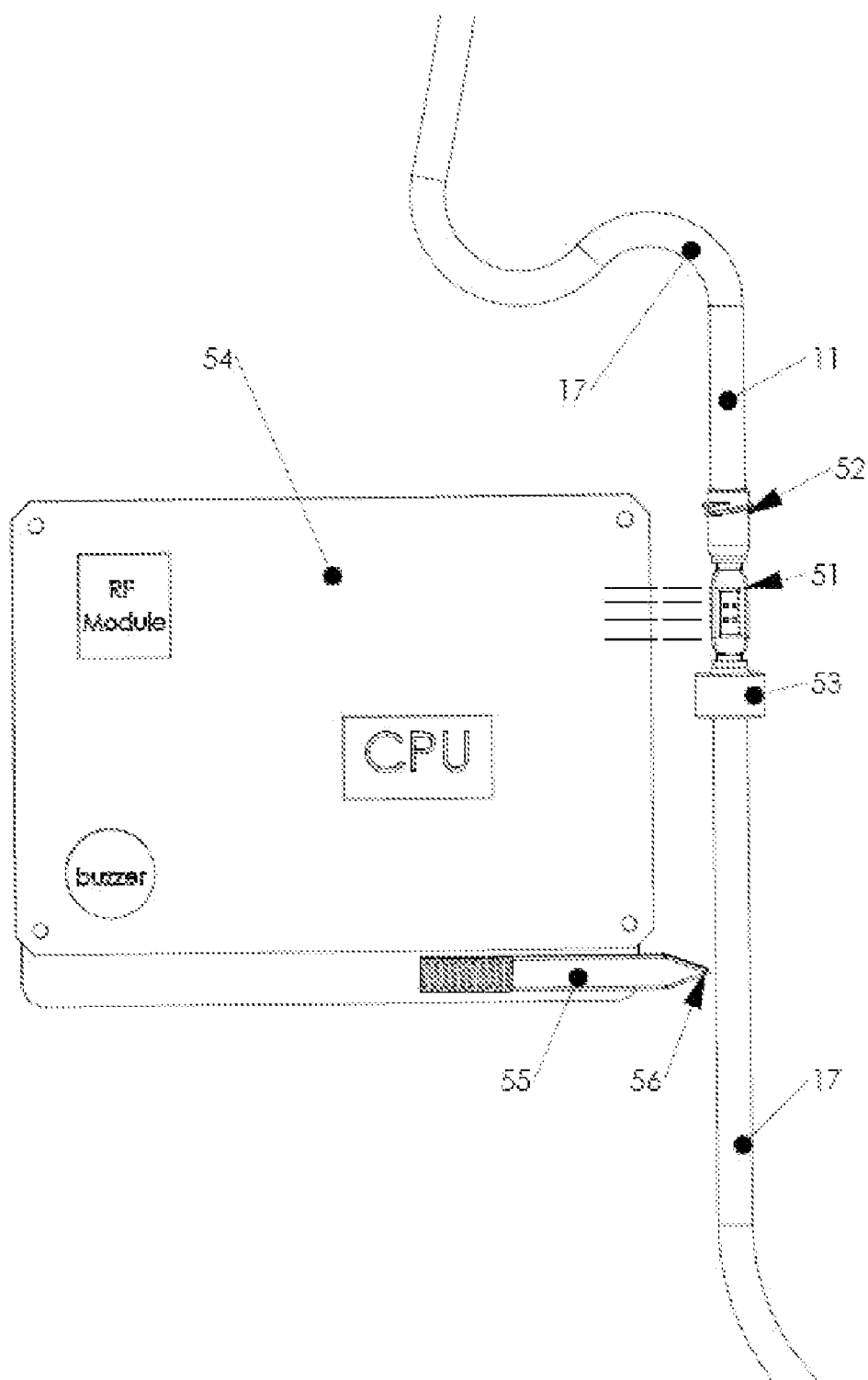
FIGS. 5a & 5b schematically depict a preferred embodiment of a flow control system.

Referring now to FIGS. 5$a$ & $b$, a preferred embodiment of flow control system is demonstrated in a schematic fashion. The sensor 51 is shown implemented in a fitting having an inlet equipped with a female Luer Lock connector and an outlet equipped with a mail Luer Lock connector. The inlet and outlet are connected to the upstream portion and downstream tube portions 17 of the disposable fluid transport device which in this case is a disposable infusion set. The fitting can be attached to the set by the manufacturer, or by the user. It can be packed with the fluid transport device or separately. The sensor communicates with a circuitry 54 (shown schematically). A movable member 55 having a first rigid pointer end 56 and a second end associated with an actuator (not shown) is controlled by the circuitry 54 such that it can be moved toward or away from the tube 17.

Figure 5B:
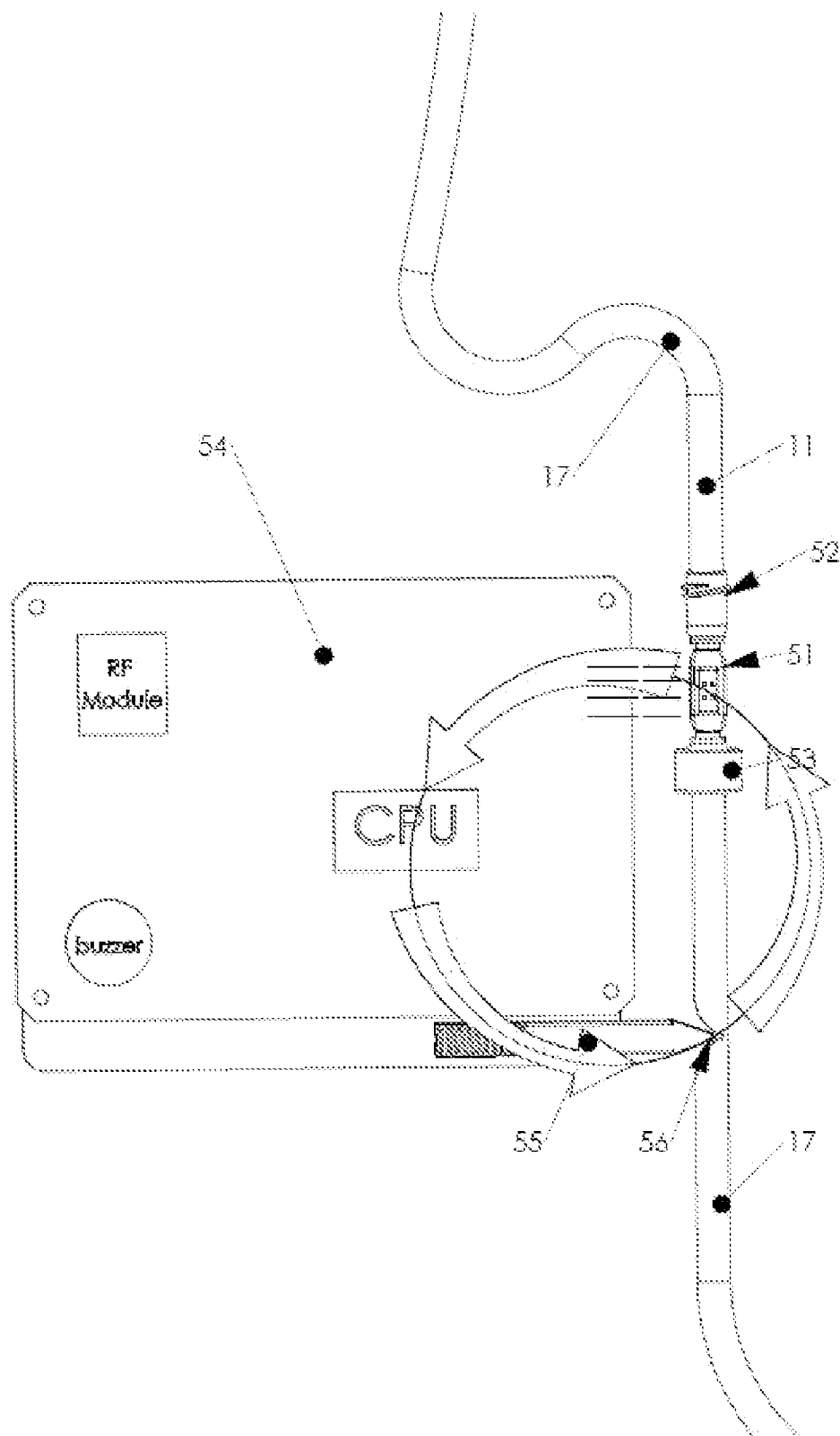

FIG. 5b demonstrates the flow control system after the control circuitry 54 causes the actuator to displace the movable member 55 toward the tube 17 and against a reciprocal rigid backing (not shown) causing it to collapse and restrict the flow passage in the tube thereby reducing the flow rate or shutting down the flow. The figure further shows schematic arrows emphasizing the ability of the system to perform a closed loop control of the flow rate by: a) sensing the flow rate in the fluid transport device, b) analyzing flow rates and comparing to a desired flow rate introduced to the system by a device or a person, and c) adjusting the flow rate by restricting the flow passage. In a further preferred embodiment the fluid transport device comprises a normally close valve and the flow control system can manipulate the valve to open per the desired flow rate.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

What is claimed is:

1. A flow rate meter, comprising:
   a. a disposable fluid transport device portion, including:
      i. a flow conduit having an inlet and an outlet, said flow conduit defining a flow channel; and
      ii. at least a first portion of a control circuitry which is operative to derive the flow rate, wherein said first portion includes a plurality of electrodes adapted to directly contact fluid when present within said conduit; and
   b. a reusable interface connector removably attachable to said disposable fluid transport device portion, said reusable interface connector including:
      i. a second portion of said control circuitry connectable to said first portion;
      ii. a communications interface for establishing feedback communication to a desired location.

2. The flow rate meter of claim 1, wherein said first portion includes two pairs of electrodes.

3. The flow rate meter of claim 2, wherein said pairs of electrodes are spaced apart axially along a length of said flow conduit.

4. The flow rate meter of claim 3, wherein at least some of said electrodes measure oxidations-reduction current.

5. The flow rate meter of claim 1, wherein said flow rate meter is a composition variation time-of-flight mass flow meter.

6. The flow rate meter of claim 1, wherein said flow rate meter comprises one of a thermo-time-of-flight mass flow meter, an electronic flow switch, and a mechanical velocity meter.

7. The flow rate meter of claim 1, wherein said communications interface comprises one of RF, IR, magnetic conduction, ultrasonic, and bi-wires.

8. The flow rate meter of claim 1, further comprising a flow control member.

9. The flow rate meter of claim 1, wherein said reusable interface connector comprises a clamp configured to attach to an infusion pole, said reusable interface connector further comprising a human machine interface.

10. The flow rate meter of claim 9, wherein said human machine interface comprises input buttons for setting parameters and functions of the reusable interface connector.

11. The flow rate meter of claim 9, wherein said human machine interface comprises at least one visual or audible indicator.

12. The flow rate meter of claim 1, wherein said flow conduit is part of dedicated tubing for an infusion pump.

13. The flow rate meter of claim 1, wherein said flow conduit is part of a disposable infusion set.

14. The flow rate meter of claim 1, wherein said control circuitry is configured to sense the flow rate through the flow conduit, analyze the flow rate, compare the flow rate to a desired flow rate, and adjust the flow rate by restricting said flow channel.

* * * * *